United States Patent [19]

Gutsche et al.

[11] 4,279,899

[45] Jul. 21, 1981

[54] BENZYLPYRIMIDINES, PROCESSES FOR THEIR MANUFACTURE, AND DRUGS CONTAINING THE SAID COMPOUNDS

[75] Inventors: Klaus Gutsche, Rellingen; Peter Scharwaechter; Wilhelm Kohlmann, both of Moorege; Gerd Kroemer, Elmshorn, all of Fed. Rep. of Germany

[73] Assignee: BASF Aktiengesellschaft, Fed. Rep. of Germany

[21] Appl. No.: 919,505

[22] Filed: Jun. 27, 1978

[30] Foreign Application Priority Data

Jul. 6, 1977 [DE] Fed. Rep. of Germany ....... 2730467

[51] Int. Cl.$^3$ ................. A61K 31/505; C07D 237/20; A61K 31/535; C07D 237/49
[52] U.S. Cl. ................................ 424/229; 424/251; 424/248.56; 544/122; 544/324; 544/325

[58] Field of Search ...................... 544/122, 324, 325; 424/248.4, 251, 248.56, 229

[56] References Cited

U.S. PATENT DOCUMENTS

| Re. 28,636 | 12/1975 | Grunberg | 424/229 |
|---|---|---|---|
| 3,049,544 | 8/1962 | Stenbuck | 260/256.4 |
| 3,178,432 | 4/1905 | Druey | 260/256.4 |
| 4,115,650 | 9/1978 | Manchand | 544/324 |

*Primary Examiner*—Donald G. Daus
*Assistant Examiner*—D. B. Springer
*Attorney, Agent, or Firm*—Keil & Witherspoon

[57] ABSTRACT

5-Benzyl-2,4-diaminopyrimidines, in which the 2-amino group is substituted, and which may or may not be substituted in the phenyl ring, and their physiologically acceptable addition salts with acids, processes for their manufacture, drugs containing these compounds, and the use of the said compounds in infectious diseases.

7 Claims, No Drawings

BENZYLPYRIMIDINES, PROCESSES FOR THEIR MANUFACTURE, AND DRUGS CONTAINING THE SAID COMPOUNDS

The present invention relates to novel benzylpyrimidines of the general formula I

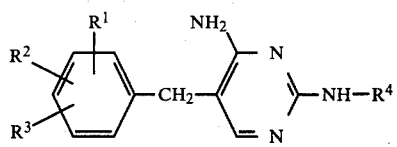

where $R^1$, $R^2$ and $R^3$, which may be identical or different, are hydrogen, methyl, methoxy or chlorine, and $R^4$ is straight-chain or branched, saturated or unsaturated, alkyl of 1 to 10 carbon atoms, whereof the carbon chain may be interrupted by from 1 to 3 oxygen atoms, and/or may form, by means of some of its carbon atoms, a cycloaliphatic ring of 5 or 6 carbon atoms, and may be substituted by a chlorine atom, a hydroxyl group or a secondary amino group, of which the nitrogen may also form part of an aliphatic cyclic amine, or is —alk—$R^5$, where alk is straight or branched alkylene of 1 to 4 carbon atoms and $R^5$ is phenyl, which may be substituted by chlorine or by alkyl of 1 to 4 carbon atoms, or is a heteroaromatic ring containing 1 or 2 oxygen and/or nitrogen atoms, and to their pharmacologically acceptable addition salts with acids conventionally used for this purpose.

Examples of substituents $R^4$ are methoxymethyl, n-butyloxymethyl, cyclohexoxymethyl, β-chloroethyloxymethyl, β-ethoxyethoxymethyl, β-methoxyethoxymethyl β-chloro-α-methyl-ethoxymethyl, β-dimethylaminoethyl, β-morpholinoethyl, β-pyrrolidinoethyl, 3-dimethylaminopropyl, allyloxymethyl, benzyloxymethyl, benzyl, 4-chlorobenzyl, phenethyl, 3-methylisoxazolyl-2-methyl, 3-tertiary butylisoxaxolyl-2-methyl and β-hydroxyethyl.

Compounds of the formula I to be mentioned particularly are those where $R^4$ is methyl which is substituted by alkoxy of 1 to 6 carbon atoms, whereof the alkyl may additionally be substituted by a chlorine atom or an alkoxy group of 1 or 2 carbon atoms which in turn may be substituted by alkoxy of 1 to 4 carbon atoms, or by allyloxy, cyclohexoxy or benzyloxy, or alkyl of 1 to 3 carbon atoms which is substituted by phenyl, chlorophenyl, hydroxyl, alkoxy of 1 to 2 carbon atoms, dialkylamino (where alkyl is of 1 or 2 carbon atoms) or pyrrolidino or morpholino, or $R^4$ is 3-alkylisoxazolyl-5-methyl, where alkyl is of 1 to 4 carbon atoms.

Preferably, the substituents $R^1$, $R^2$ and $R^3$ are in the 3-, 4- and 5-positions of the benzene ring.

Preferred compounds of the formula I are those where $R^4$ is -alk-O—$R^6$, $R^6$ being hydrogen, straight-chain or branched-chain alkyl of 1 to 6 carbon atoms, which alkyl may be substituted by chlorine or lower alkoxy of 1 to 4 carbon atoms, cyclohexyl, phenyl or benzyl and alk is straight-chain or branched-chain alkylene of 1 to 4 carbon atoms.

Those compounds of the formula I where $R^1$, $R^2$ and $R^3$ are methoxy are very particularly preferred.

The compounds of the formula I and their salts are antimicrobially active in diseases caused by bacteria and protozoa and, when combined with sulfonamides, potentiate their antimicrobial action. They may be used, for example, in bacterial infections of the respiratory organs, digestive organs and urinary tract, in infections of the throat, nose and ears, in systemic infections in general, and in malaria.

Examples of suitable sulfonamides are 2-sulfanilamidopyrimidine, 2-sulfanilamido-5-methoxypyrimidine, 4-sulfanilamido-2,6-dimethoxypyrimidine, 3-sulfanilamido-5-methylisoxazole, 2-sulfanilamido-4,5-dimethyloxazole, 3-sulfanilamido-6-methoxypyridazine, 4-sulfanilamido-2,6-dimethylpyrimidine, 4-sulfanilamido-5,6-dimethoxypyrimidine and 2-sulfanilamido-3-methoxypyrazine.

Examples of conventional acids used to form pharmacologically acceptable salts are hydrochloric acid, sulfuric acid, phosphoric acid, nitric acid, acetic acid, lactic acid, tartaric acid and citric acid.

However, the inorganic acids mentioned, especially hydrochloric acid and sulfuric acid, are preferred; they form salts which crystallize particularly well with the compounds according to the invention.

The compounds of the formula I and their salts can be combined with the sulfonamides, mentioned by way of example, in various ratios; the ratio of the former to the latter may be from 1:10 to 5:1. However, preferred ratios are from 1:1 to 1:5. As a rule, a suitable dosage is from 20 to 500 mg of an active compound of the formula I.

The compounds according to the invention, of the formula I, are prepared by the following methods:

(a) A compound of the general formula II

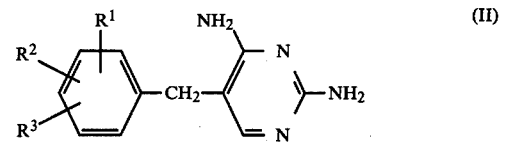

where $R^1$, $R^2$ and $R^3$ have the same meanings as in formula I, is reacted with a compound of the general formula III

Hal—$R^4$      (III)

where $R^4$ has the same meaning as in formula I, and Hal is halogen, especially Cl or Br, or (b) a compound of the general formula IV

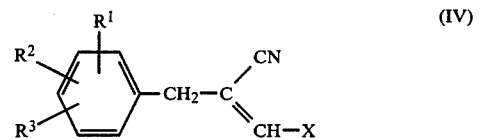

where $R^1$, $R^2$ and $R^3$ have the same meanings as in formula I and X is a leaving group, is reacted with a compound of the general formula V

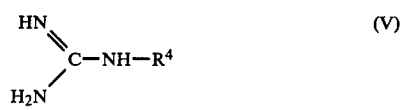

where $R^4$ has the same meaning as in formula I, or (c) a compound of the general formula VI

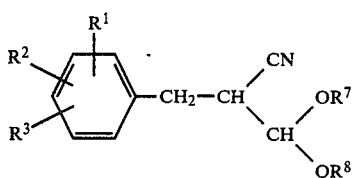

where $R^1$, $R^2$ and $R^3$ have the same meanings as in formula I and $R^7$ and $R^8$ are lower alkyl, is reacted with a compound of the general formula V.

Processes (a) to (c) are not intended to imply any limitation on the numerous conventional methods of synthesis which involve a cyclization reaction with a compound of the general formula V.

In process (a), the reaction is in general carried out in an aprotic diluent, eg. dioxane, tetrahydrofuran, benzene, chlorobenzene, chloroform or pyridine, at from 0° to 200° C. depending on the reactivity of the compound of the general formula III.

In process (b), the reaction is carried out in an alcohol, preferably methanol or ethanol, or in dimethylformamide or dimethylsulfoxide as the solvent, at from 50° to 150° C. Temperatures of about 150° C. are required if the leaving group X is an aliphatic amino group which reacts sluggishly. The leaving group in the formula IV is alkoxy, preferably methoxy or ethoxy, or secondary aliphatic amino, preferably morpholino or dimethylamino, or primary aromatic amino, preferably anilino, or imidazol-1-yl.

To demonstrate the action of the compounds according to the invention, the latter were tested in animal experiments, using the Aronson sepsis model, infection being carried out with *Streptococcus agalactiae*, and were compared with the conventional drug Trimethoprim. Groups of 30 female mice were infected with a lethal dose of *Streptococcus agalactiae* 7941 and 2 hours after infection were treated with a mixture of 300 mg of 2-sulfanilamido-4,5-dimethyl-oxazole + 60 mg of one of the compounds according to the invention. In addition to an untreated control group, a second group was treated with a mixture - serving as a reference substance - of 300 mg of 2-sulfanilamido-4,5-dimethyloxazole + 60 mg of Trimethoprim. After 44 hours, the number of surviving animals was determined and divided by the number of survivors from the group treated with the reference substance. The numerical value thus obtained (the Trimethoprim factor) is a measure of the action of the compounds according to the invention compared to Trimethoprim. Accordingly, F = 2 means that the compound is twice as active as Trimethoprim. The Table which follows shows that the compounds according to the invention exhibit up to a 3-fold superiority over Trimethoprim.

TABLE I

General formula

| No. | $R^1$ | $R^2$ | $R^3$ | $R^5$ | F |
|---|---|---|---|---|---|
| 1 | (3)-OCH$_3$ | (4)-OCH$_3$ | (5)-OCH$_3$ | —OCH$_3$ | 1.25 |
| 2 | (3)-OCH$_3$ | (4)-OCH$_3$ | (5)-OCH$_3$ | —O—C$_3$H$_7$(n) | 2,50 |
| 3 | (3)-OCH$_3$ | (4)-OCH$_3$ | (5)-OCH$_3$ | —O—⟨H⟩ (cyclohexyl) | 1,60 |
| 4 | (3)-OCH$_3$ | (4)-OCH$_3$ | (5)-OCH$_3$ | —O—CH$_2$—phenyl | 2,00 |
| 5 | (3)-OCH$_3$ | (4)-OCH$_3$ | (5)-OCH$_3$ | —O—C$_2$H$_4$·Cl | 1.00 |
| 6 | (3)-OCH$_3$ | (4)-OCH$_3$ | (5)-OCH$_3$ | —CH$_2$—phenyl | 2.00 |
| 7 | (3)-OCH$_3$ | (4)-OCH$_3$ | (5)-OCH$_3$ | —O—(CH$_2$)$_5$·CH$_3$ | 1.10 |
| 8 | (3)-OCH$_3$ | (4)-OCH$_3$ | (5)-OCH$_3$ | —CH—CH$_2$ | 1.33 |
| 9 | (3)-OCH$_3$ | (4)-OCH$_3$ | (5)-OCH$_3$ | —O—CH$_2$—CH=CH$_2$ | 1.64 |
| 10 | (3)-OCH$_3$ | (4)-OCH$_3$ | (5)-OCH$_3$ | —CH$_2$—N(CH$_3$)$_2$ | 1.10 |
| 11 | (3)-OCH$_3$ | (4)-OCH$_3$ | (5)-OCH$_3$ | —CH$_2$—N(pyrrolidinyl, H) | 1.50 |
| 12 | (3)-OCH$_3$ | (4)-OCH$_3$ | (5)-OCH$_3$ | —CH$_2$—N(morpholino) | 2.00 |
| 13 | (3)-OCH$_3$ | (4)-OCH$_3$ | (5)-OCH$_3$ | —CH$_2$—O—C$_2$H$_5$ | 3.00 |
| 14 | (3)-OCH$_3$ | (4)-OCH$_3$ | (5)-OCH$_3$ | —CH$_2$—CH$_2$—O—C$_2$H$_5$ | 1.00 |
| 15 | (3)-OCH$_3$ | (4)-OCH$_3$ | (5)-OCH$_3$ | —CH$_2$—CH$_2$—N(C$_2$H$_5$)$_2$ | 1.50 |

TABLE I-continued

General formula $$\text{R}^1\text{-}\text{R}^2\text{-}\text{R}^3\text{-C}_6\text{H}_2\text{-CH}_2\text{-C}(=\text{CH-N})\text{-C}(\text{NH}_2)=\text{N-C(NH-CH}_2\text{-R}^5) \cdot \text{HCl}$$

| No. | R¹ | R² | R³ | R⁵ | F |
|-----|-----|-----|-----|-----|------|
| 16 | (3)-OCH₃ | (4)-OCH₃ | (5)-OCH₃ | 3-methyl-isoxazol-5-yl | 1.10 |
| 17 | H | (4)-OCH₃ | H | —O—CH₂—CH=CH₂ | 1.67 |
| 18 | (3)-OCH₃ | (4)-OCH₃ | H | —O—CH₂—C₆H₅ | 1.17 |
| 19 | 2-Cl | H | H | —O—CH₂—CH₂—CH₂—Cl | 1.50 |

Accordingly, the present invention also relates to chemotherapeutic agents which contain a compound of the formula I, in particular in combination with a sulfonamide, as the active ingredient, together with conventional carriers and excipients, and to the use of the compounds of the formula I as sulfonamide potentiators.

The chemotherapeutic agents or formulations are prepared in the conventional manner, using the conventional carriers or excipients and conventional pharmacological assistants, in accordance with the desired route of administration.

The preferred formulations are those suitable for oral administration. Examples are tablets, film tablets, dragees, capsules, pills, powders, solutions and suspensions.

EXAMPLE 1

2-Methoxymethylamino-4-amino-5-(3,4,5-trimethoxybenzyl)-pyrimidine hydrochloride 5.8 g of 2,4-diamino-5-(3,4,5-trimethoxybenzyl)-pyrimidine were dissolved in 60 ml of pyridine at 60° C. and 3.0 ml of chlorodimethyl ether were added dropwise to the solution at the same temperature. The pyridine was then distilled off under reduced pressure and the residue was recrystallized from 250 ml of ethanol. 5.5 g (74% of theory) of 2-methoxymethylamino-4-amino-5-(3,4,5-trimethoxybenzyl)-pyrimidine. HCl of melting point 227° C. were obtained.

EXAMPLE 2

2-Cyclohexoxymethylamino-4-amino-5-(3,4,5-trimethoxybenzyl)-pyrimidine hydrochloride 5.8 g of 2,4-diamino-5-(3,4,5-trimethoxybenzyl)-pyrimidine were dissolved in 100 ml of dioxane at 80° C. and 2.97 g of chloromethyl cyclohexyl ether were added dropwise to the solution. After completion of the addition, the mixture was stirred for 30 minutes at 90° C. The precipitate obtained after cooling was recrystallized from methylglycol, with addition of ether. 6.8 g (77% of theory) of 2-cyclohexoxymethylamino-4-amino-5-(3,4,5-trimethoxybenzyl)-pyrimidine.HCl of melting point 208° C. were obtained.

The following were also prepared by the methods of Examples 1 and 2:

3. 2-Ethoxymethylamino-4-amino-5-(3,4,5-trimethoxybenzyl)-pyrimidine.HCl of melting point 206° C., from 2,4-diamino-5-(3,4,5-trimethoxybenzyl)-pyrimidine and chloromethyl ethyl ether.

4. 2-n-Propoxymethylamino-4-amino-5-(3,4,5-trimethoxybenzyl)-pyrimidine.HCl of melting point 249° C., from 2,4-diamino-5-(3,4,5-trimethoxybenzyl)-pyrimidine and chloromethyl n-propyl ether.

5. 2-n-Butoxymethylamino-4-amino-5-(3,4,5-trimethoxybenzyl)-pyrimidine.HCl of melting point 235° C., from 2,4-diamino-5-(3,4,5-trimethoxybenzyl)-pyrimidine and chloromethyl n-butyl ether.

6. 2-n-Hexoxymethylamino-4-amino-5-(3,4,5-trimethoxybenzyl)-pyrimidine.HCl of melting point 228° C., from 2,4-diamino-5-(3,4,5-trimethoxybenzyl)-pyrimidine and chloromethyl n-hexyl ether.

7. 2-Allyloxymethylamino-4-amino-5-(3,4,5-trimethoxybenzyl)-pyrimidine.HCl of melting point 220°–222° C., from 2,4-diamino-5-(3,4,5-trimethoxybenzyl)-pyrimidine and chloromethyl allyl ether.

8. 2-(β-Chloroethoxymethylamino)-4-amino-5-(3,4,5-trimethoxybenzyl)-pyrimidine.HCl of melting point 218° C., from 2,4-diamino-5-(3,4,5-trimethoxybenzyl)-pyrimidine and chloromethyl β-chloroethyl ether.

9. 2-(2-Chloro-1-methyl-ethoxymethylamino)-4-amino-5-(3,4,5-trimethoxybenzyl)-pyrimidine.HCl of melting point 230° C., from 2,4-diamino-5-(3,4,5-trimethoxybenzyl)-pyrimidine and chloromethyl 2-chloro-1-methylethyl ether.

10. 2-Benzyloxymethylamino-4-amino-5-(3,4,5-trimethoxybenzyl)-pyrimidine.HCl of melting point 227° C., from 2,4-diamino-5-(3,4,5-trimethoxybenzyl)-pyrimidine and chloromethyl benzyl ether.

11. 2-(β-Methoxyethoxymethylamino)-4-amino-5-(3,4,5-trimethoxybenzyl)-pyrimidine.HCl of melting point 226° C., from 2,4-diamino-5-(3,4,5-trimethoxybenzyl)-pyrimidine and chloromethyl β-methoxyethyl ether.

12. 2-(β-Ethoxyethoxymethylamino)-4-amino-5-(3,4,5-trimethoxybenzyl)-pyrimidine.HCl of melting point 216° C., from 2,4-diamino-5-(3,4,5-trimethoxybenzyl)-pyrimidine and chloromethyl β-ethoxyethyl ether.

13. 2-Cyclohexoxymethylamino-4-amino-5-(4-methoxybenzyl)-pyrimidine.HCl of melting point 297° C., from 2,4-diamino-5-(4-methoxy)-pyrimidine and chloromethyl cyclohexyl ether.

14. 2-Benzyloxymethylamino-4-amino-5-(3,4-dimethoxybenzyl)-pyrimidine.HCl of melting point 182° C., from 2,4-diamino-5-(3,4-dimethoxybenzyl)-pyrimidine and chloromethyl benzyl ether.

15. 2-(β-Chloroethoxymethylamino)-4-amino-5-(2-chlorobenzyl)-pyrimidine.HCl of melting point 222° C., from 2,4-diamino-5-(2-chlorobenzyl)-pyrimidine and chloromethyl β-chloroethyl ether.

16. 2-(β-Ethoxyethoxymethylamino)-4-amino-5-(4-chlorobenzyl)-pyrimidine.HCl of melting point 218° C., from 2,4-diamino-5-(4-chlorobenzyl)-pyrimidine and chloromethyl β-ethoxyethyl ether.

17. 2-Allyloxymethylamino-4-amino-5-(2,4-dimethoxybenzyl)-pyrimidine.HCl of melting point 200° C., from 2,4-diamino-5-(2,4-dimethoxybenzyl)-pyrimidine and chloromethyl allyl ether.

18. 2-(3-Methylisoxazol-5-yl)-methylamino-4-amino-5-(3,4,5-trimethoxybenzyl)-pyrimidine.HCl of melting point 290° C., from 2,4-diamino-5-(3,4,5-trimethoxybenzyl)-pyrimidine and 3-methyl-5-chloromethyl-isoxazole.

19. 2-(3-Ethylisoxazol-5-yl)-methylamino-4-amino-5-(3,4,5-trimethoxybenzyl)-pyrimidine.HCl of melting point 291° C., from 2,4-diamino-5-(3,4,5-trimethoxybenzyl)-pyrimidine and 3-ethyl-5-chloromethyl-isoxazole.

20. 2-(3-Isopropylisoxazol-5-yl)-methylamino-4-amino-5-(3,4,5-trimethoxybenzyl)-pyrimidine.HCl of melting point 290° C., from 2,4-diamino-5-(3,4,5-trimethoxybenzyl)-pyrimidine and 3-isopropyl-5-chloromethyl-isoxazole.

21. 2-(3-Tertiary butylisoxazol-5-yl)-methylamino-4-amino-5-(3,4,5-trimethoxybenzyl)-pyrimidine.HCl of melting point 280° C., from 2,4-diamino-5-(3,4,5-trimethoxybenzyl)-pyrimidine and 3-tertiary butyl-5-chloromethylisoxazole.

EXAMPLE 22

2-Benzylamino-4-amino-5-(3,4,5-trimethoxybenzyl)-pyrimidine 5 g of α-anilino-β-(3,4,5-trimethoxybenzyl)-acrylonitrile, 5.9 g of benzylguanidinium sulfate and 1.6 g of sodium methylate in 50 ml of ethanol were refluxed for 4 hours. 10 ml of water were then added to the mixture and after cooling the crystals were filtered off and washed with water.

After recrystallizing the product from isopropanol, 4.1 g (72% of theory) of 2-benzylamino-4-amino-5-(3,4,5-trimethoxybenzyl)-pyrimidine of melting point 135° C. were obtained.

The following were obtained by the method described in Example 22:

23. 2-Allylamino-4-amino-5-(3,4,5-trimethoxybenzyl)-pyrimidine, of melting point 132° C., by using allylguanidine sulfate.

24. 2-(Phenethyl-β-amino)-4-amino-5-(3,4,5-trimethoxybenzyl)-pyrimidine, of melting point 124° C., by using phenethylguanidine sulfate.

25. 2-(4-Chlorobenzylamino)-4-amino-5-(3,4,5-trimethoxybenzyl)-pyrimidine, of melting point 143° C., by using 4-chlorobenzylguanidine sulfate.

26. 2-(β-Dimethylaminoethylamino)-4-amino-5-(3,4,5-trimethoxybenzyl)-pyrimidine, of melting point 139° C., by using β-dimethylaminoethylguanidine sulfate.

27. 2-(β-Morpholinoethylamino)-4-amino-5-(3,4,5-trimethoxybenzyl)-pyrimidine, of melting point 140° C., by using β-morpholinoethylguanidine sulfate.

28. 2-(β-Pyrrolidinoethylamino)-4-amino-5-(3,4,5-trimethoxybenzyl)-pyrimidine, of melting point 130° C., by using β-pyrrolidinoethylguanidine sulfate.

29. 2-(3-Dimethylamino-n-propyl-1-amino)-4-amino-5-(3,4,5-trimethoxybenzyl)-pyrimidine, of melting point 139° C., by using 3-dimethylamino-n-propyl-1-guanidine sulfate.

30. 6.4 g of α-cyano-β-(3,4,5-trimethoxyphenyl)-propionaldehyde dimethylacetal, 3 g of β-hydroxyethylguanidine sulfate and 1.1 g of sodium methylate in 100 ml of ethanol were refluxed for 5 hours. The ethanol was then distilled off and the residue was dissolved in 100 ml of water. On extracting the solution with chloroform, 3.4 g (50% of theory) of 2-(β-hydroxyethylamino)-4-amino-5-(3,4,5-trimethoxybenzyl)-pyrimidine were obtained, melting at 146° C. after recrystallization from isopropanol.

31. 5.6 g of α-(3,4,5-trimethoxybenzyl)-β-dimethylamino-acrylonitrile, 3.8 g of β-ethoxyethylguanidine sulfate and 2 g of sodium methylate in 100 ml of dimethylsulfoxide were stirred for 3 hours at 150° C. The dimethylsulfoxide was then distilled off under reduced pressure and 100 ml of water were added to the residue. The oily product was extracted with chloroform and after concentrating the extracts the residue was repeatedly recrystallized from a mixture of ethyl acetate and isopropyl ether. This gave 1.4 g (20% of theory) of 2-(β-ethoxyethylamino)-4-amino-5-(3,4,5-trimethoxybenzyl)-pyrimidine of melting point 147° C.

32. 12 g of β-imidazol-1-yl-propionitrile, 6 g of sodium methylate and 19.6 g of 3,4,5-trimethoxybenzaldehyde in 200 ml of methanol were refluxed for 12 hours. 37 g of (3-ethoxy-n-prop-1-yl)-guanidine sulfate and a further 6 g of sodium methylate were then added, the methanol was distilled off slowly and the residue was stirred for 2 hours at 110° C. The reaction mixture was stirred with 200 ml of water and semi-solid product was extracted with chloroform. The residue from the chloroform extract was recrystallized from a mixture of ethyl acetate and isopropyl ether. This gave 12 g (32% of theory) of 2-(3-ethoxy-n-propyl-1-amino)-4-amino-5-(3,4,5-trimethoxybenzyl)-pyrimidine of melting point 118° C.

33. 2-[β(β-Methoxyethoxy)-ethoxymethylamino]-4-amino-5-(3,4,5-trimethoxybenzyl)-pyrimidine hydrochloride of melting point 206°–209° C. was obtained, by the method described in Example 1, from Trimethoprim and β-(β-methoxyethoxy)-ethyl chloromethyl ether.

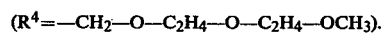

(R⁴=—CH₂—O—C₂H₄—O—C₂H₄—OCH₃).

34. 2-[β(β-n-Butoxyethoxy)-ethoxymethylamino]-4-amino-5-(3,4,5-trimethoxy)-benzylpyrimidine hydrochloride of melting point 213° C. was obtained, by the method described in Example 1, from Trimethoprim and β-(β-n-butoxyethoxy)-ethyl chloromethyl ether.

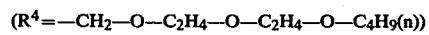

(R⁴=—CH₂—O—C₂H₄—O—C₂H₄—O—C₄H₉(n))

FORMULATION EXAMPLES (1).

400 mg of 2-sulfanilamido-4,5-dimethyloxazole
80 mg of 2-benzyloxymethylamino-4-amino-5-(3,4,5-trimethoxybenzyl)-pyrimidine
20 mg of corn starch
10 mg of gelatin
8 mg of talc
2 mg of magnesium stearate
20 mg of Primojel The active ingredients are mixed with corn starch and granulated, using the aqueous gelatin solution. The dry granules are sieved and mixed with the additives. This mixture is tableted in the conventional manner.

(2).

160 mg of 2-sulfanilamido-5-methoxy-pyrimidine
80 mg of 2-n-hexoxymethylamino-4-amino-5-(3,4,5-trimethoxybenzyl)-pyrimidine
5 mg of gelatin
30 mg of corn starch
4 mg of talc
1 mg of magnesium stearate The active ingredients are granulated, using the aqueous gelatin solution, and the dried granules are mixed with corn starch, talc and magnesium stearate. This mixture is tableted in the conventional manner.

(3).

4.00 g of 2-sulfanilamido-5-methoxy-pyrimidine
2.00 g of 2-n-hexoxymethylamino-4-amino-5-(3,4,5-trimethoxybenzyl)-pyrimidine
1.9 g of Tylose C 30
30.0 g of sugar
10.0 g of glycerol
2.5 g of bentonite
0.06 g of flavoring
0.04 g of Nipagin M
0.06 g of Nipasol sodium
ad 100.00 g demineralized water The very finely milled active ingredients are suspended in the aqueous Tylose mucilage. All the other ingredients are then added successively, whilst stirring. Finally, the mixture is made up to 100.0 g with water.

We claim:

1. A benzylpyrimidine of the formula

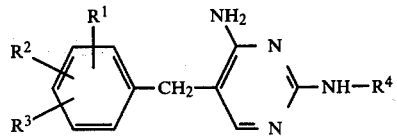

where $R^1$, $R^2$, and $R^3$, which may be identical or different, are in the 3-, 4-, and 5-positions of the benzene ring, and each may be selected from the group consisting of hydrogen, methyl, methoxy or chlorine, and $R^4$ is methyl which is substituted by alkoxy of 1 to 6 carbon atoms, wherein the alkyl may additionally be substituted by a chlorine atom or an alkoxy group of 1 or 2 carbon atoms which in turn may be substituted by alkoxy of 1 to 4 carbon atoms, or by allyloxy, cyclohexoxy, or benzyloxy, or $R^4$ is allyl or alkyl of 1 to 3 carbon atoms which is substituted by phenyl, chlorophenyl, hydroxyl, alkoxy of 1 or 2 carbon atoms, dialkylamino (where alkyl is of 1 or 2 carbon atoms), pyrrolidino or morpholino, or $R^4$ is 3-alkylisoxazolyl-5-methyl, wherein the alkyl is 1 to 4 carbon atoms.

2. A benzylpyrimidine according to claim 1 in which $R^1$, $R^2$, and $R^3$ are each —OCH$_3$, and $R^4$ is —CH$_2$—O—C$_3$H$_7$(n).

3. A benzylpyrimidine according to claim 1 in which $R^1$, $R^2$, and $R^3$ are each —OCH$_3$, and $R^4$ is

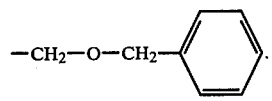

4. A benzylpyrimidine according to claim 1 in which $R^1$, $R^2$, and $R^3$ are each —OCH$_3$, and $R^4$ is

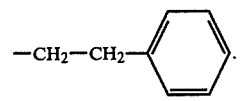

5. A benzylpyrimidine according to claim 1 in which $R^1$, $R^2$, and $R^3$ are each —OCH$_3$, and $R^4$ is

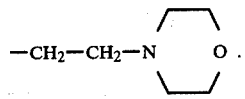

6. A benzylpyrimidine according to claim 1 in which $R^1$, $R^2$, and $R^3$ are each —OCH$_3$, and $R^4$ is —CH$_2$—CH$_2$—O—C$_2$H$_5$.

7. An antimicrobial active composition consisting essentially of a benzylpyrimidine according to claim 1, with or without a sulfoamide, and a non-toxic pharmaceutically acceptable solid or liquid carrier.

* * * * *